(12) United States Patent
Spigone et al.

(10) Patent No.: US 10,705,075 B2
(45) Date of Patent: Jul. 7, 2020

(54) APPARATUS AND METHOD FOR CONTROLLABLY POPULATING A CHANNEL WITH CHARGE CARRIERS

(71) Applicant: Nokia Technologies Oy, Espoo (FI)

(72) Inventors: Elisabetta Spigone, Cambridge (GB); Piers Andrew, Cambridge (GB)

(73) Assignee: Nokia Technologies Oy, Espoo (FI)

(*) Notice: Subject to any disclaimer, the term of this patent is extended or adjusted under 35 U.S.C. 154(b) by 18 days.

(21) Appl. No.: 15/511,557

(22) PCT Filed: Sep. 16, 2015

(86) PCT No.: PCT/FI2015/050620
§ 371 (c)(1),
(2) Date: Mar. 15, 2017

(87) PCT Pub. No.: WO2016/042210
PCT Pub. Date: Mar. 24, 2016

(65) Prior Publication Data
US 2017/0261500 A1    Sep. 14, 2017

(30) Foreign Application Priority Data
Sep. 18, 2014  (EP) .................... 14185442

(51) Int. Cl.
*G01N 33/542* (2006.01)
*B82Y 15/00* (2011.01)
(Continued)

(52) U.S. Cl.
CPC .............. *G01N 33/542* (2013.01); *B82Y 5/00* (2013.01); *B82Y 15/00* (2013.01);
(Continued)

(58) Field of Classification Search
CPC .. G01N 33/542; G01N 27/4146; B82Y 15/00; B82Y 5/00; B82Y 10/00;
(Continued)

(56) References Cited

U.S. PATENT DOCUMENTS

2005/0064604 A1* 3/2005 Bohmann ............ B82Y 30/00
436/525
2005/0287560 A1* 12/2005 Garimella ........... B01J 19/0046
435/6.12
(Continued)

FOREIGN PATENT DOCUMENTS

CN       1842704 A    10/2006
CN     101701927 A     5/2010
(Continued)

OTHER PUBLICATIONS

Cui et al., Self-Assembly of Quantum Dots and Carbon Nanotubes for Ultrasensitive DNA and Antigen Detection, 2008, Analytical Chemistry, vol. 80, pp. 7996-8001.*
(Continued)

*Primary Examiner* — Melanie Brown
(74) *Attorney, Agent, or Firm* — Harrington & Smith

(57) ABSTRACT

An apparatus comprising: a channel (4) configured to conduct charge carriers; and a charge carrier generator (22) configured to generate charge carriers for populating the channel, wherein the charge carrier generator is configured for resonance energy transfer (FRET). The charge carrier generator may be a nanoparticle or quantum dot (22), functionalised with at least one moiety (28A, 28B) to enable detection of an analyte. The charge carrier generator may also be a nanoparticle or quantum dot (22) configured to photo-generate charge carriers. The channel (4) may be made of a material having a very high carrier mobility like graphene or carbon nanotubes.

11 Claims, 4 Drawing Sheets

(51) Int. Cl.
| | |
|---|---|
| *B82Y 5/00* | (2011.01) |
| *G01N 27/414* | (2006.01) |
| *H02J 50/30* | (2016.01) |
| *H01L 31/0352* | (2006.01) |
| *H01L 31/113* | (2006.01) |
| *H01L 29/775* | (2006.01) |
| *H01L 29/16* | (2006.01) |
| *H01L 29/12* | (2006.01) |
| *B82Y 10/00* | (2011.01) |
| *H01L 29/06* | (2006.01) |
| *B82Y 20/00* | (2011.01) |
| *B82Y 40/00* | (2011.01) |

(52) U.S. Cl.
CPC . *G01N 27/4146* (2013.01); *H01L 31/035218* (2013.01); *H01L 31/1136* (2013.01); *H02J 50/30* (2016.02); *B82Y 10/00* (2013.01); *B82Y 20/00* (2013.01); *B82Y 40/00* (2013.01); *H01L 29/0673* (2013.01); *H01L 29/127* (2013.01); *H01L 29/1606* (2013.01); *H01L 29/775* (2013.01); *Y10S 977/774* (2013.01); *Y10S 977/89* (2013.01); *Y10S 977/957* (2013.01)

(58) Field of Classification Search
CPC .......... B82Y 20/00; B82Y 40/00; H02J 50/30; H01L 31/035218; H01L 31/1136; H01L 29/775; H01L 29/1606; H01L 29/127; H01L 29/0673
See application file for complete search history.

(56) References Cited

U.S. PATENT DOCUMENTS

| | | | |
|---|---|---|---|
| 2006/0228723 A1* | 10/2006 | Bradley .............. | B01L 3/50857 435/6.11 |
| 2007/0231790 A1* | 10/2007 | Su ........................ | C12Q 1/6825 435/5 |
| 2009/0142852 A1* | 6/2009 | Friedrich ........... | G01N 21/6428 436/164 |
| 2012/0214172 A1 | 8/2012 | Chen et al. | |
| 2013/0032782 A1 | 2/2013 | Gerasimos et al. | |
| 2013/0140518 A1* | 6/2013 | Jain .................... | G01N 27/4145 257/12 |
| 2013/0306934 A1 | 11/2013 | Lee et al. | |

FOREIGN PATENT DOCUMENTS

| | | |
|---|---|---|
| CN | 101935012 A | 1/2011 |
| CN | 102565034 A | 7/2012 |
| CN | 104024146 A | 9/2014 |
| EP | 2211178 A1 | 7/2010 |
| JP | 2003-202337 A | 7/2003 |
| WO | 2011102885 | 8/2011 |
| WO | 2013036278 | 3/2013 |
| WO | 2013096692 | 6/2013 |
| WO | 2014/066902 A1 | 5/2014 |
| WO | 2014/068554 A1 | 5/2014 |

OTHER PUBLICATIONS

Pan et al., Effects of Carbon Nanotubes on Photoluminescence Properties of Quantum Dots, Journal of Physical Chemistry C, 2008 , 112, pp. 939-944.*

International Search Report and Written Opinion received for corresponding Patent Cooperation Treaty Application No. PCT/FI2015/050620, dated Jan. 7, 2016 15 pages.

Peng Huang et al. "Simultaneous Detection of Multi-DNAs and Antigens Based on Self-Assembly of Quantum Dots and Carbon Nanotubes" in Carbon Nantubes—Growth and Applications, Aug. 9, 2011, InTech, XP055159678, ISBN: 978-9-53-307566-2, DOI 10.5772/16654.

Medintz et al., "Self-Assembled Nanoscale Biosensors Based on Quantum Dot FRET Donors", Nature Materials, vol. 2, Sep. 2003, pp. 630-638.

"Fluorescence Resonance Energy Transfer (FRET)", Netherlands Cancer Institute, Retrieved on Mar. 22, 2017, Webpage available at :http://research.nki.nl/jalinklab/Homepage%20Phys&ImgGrp%20FRET.htm.

"Fluorescence Resonance Energy Transfer (FRET)—Note 1.2", Thermofisher Scientific, Retrieved on May 10, 2017, Webpage available at : http://www.b2b.invitrogen.com/site/us/en/home/References/Molecular-Probes-The-Handbook/Technical-Notes-and-Product-Highlights/Fluorescence-Resonance-Energy-Transfer-FRET.html.

Zhang et al., "Single-Quantum-Dot-Based DNA Nanosensor", Nature materials, vol. 4, Nov. 2005, pp. 826-831.

Kim et al., "Analysis of Protease Activity Using Quantum Dots and Resonance Energy Transfer", Theranostics, vol. 2, No. 2, 2012, pp. 127-138.

Zhang et al., "Quantum Dot Enabled Molecular Sensing and Diagnostics", Theranostics, vol. 2, No. 7, Jul. 4, 2012, pp. 631-654.

Konstantatos et al., "Hybrid Graphene—Quantum Dot Phototransistors With Ultrahigh Gain", Nature Nanotechnology, vol. 7, Jun. 2012, pp. 363-368.

Martins et al., "New Insights on Optical Biosensors: Techniques, Construction and Application", State of the Art in Biosensors—General Aspects INTECH, 2013, pp. 111-139.

Dong et al., "Fluorescence Resonance Energy Transfer between Quantum Dots and Graphene Oxide for Sensing Biomolecules", Analytical Chemistry, vol. 82, No. 13, Jul. 1, 2010, pp. 5511-5517.

Extended European Search Report received for corresponding European Patent Application No. 14185442.2, dated Jan. 12, 2015, 10 pages.

Office action received for corresponding Chinese Patent Application No. 201580062271.2, dated Mar. 30, 2018, 6 pages of office action and no page of translation available.

Office action received for corresponding Japanese Patent Application No. 2017-515202, dated Apr. 17, 2018, 2 pages of office action and 2 pages of translation available.

Qian et al., "DNA Nanosensor Based on Biocompatible Graphene Quantum Dots and Carbon Nanotubes", Biosensors and Bioelectronics, vol. 60, Oct. 15, 2014, pp. 64-70.

* cited by examiner

APPARATUS AND METHOD FOR CONTROLLABLY POPULATING A CHANNEL WITH CHARGE CARRIERS

RELATED APPLICATION

This application was originally filed as PCT Application No. PCT/FI2015/050620 filed Sep. 16, 2015, which claims priority benefit from EP Application No. 14185442.2, filed Sep. 18, 2014.

TECHNOLOGICAL FIELD

Embodiments of the present invention relate to an apparatus and method for controllably populating a channel with charge carriers.

BACKGROUND

Some electronic apparatus are configured to controllably populate a channel with charge carriers. The subsequent change in the electrical conductivity of the channel can then be measured.

Such electronic apparatus may, for example, be used a photo-detectors.

It would be desirable to use an apparatus to detect physical analytes such as, for example, organic or inorganic compounds.

BRIEF SUMMARY

According to various, but not necessarily all, embodiments of the invention there is provided an apparatus comprising: a channel configured to conduct charge carriers; and a charge carrier generator configured to generate charge carriers for populating the channel, wherein the charge carrier generator is configured for resonance energy transfer.

According to various, but not necessarily all, embodiments of the invention there is provided a method comprising: modifying a population of a majority charge carriers in a channel by modifying resonance energy transfer by a charge carrier generator that populates a channel with charge carriers.

According to various, but not necessarily all, embodiments of the invention there is provided examples as claimed in the appended claims.

BRIEF DESCRIPTION

For a better understanding of various examples that are useful for understanding the brief description, reference will now be made by way of example only to the accompanying drawings in which.

DETAILED DESCRIPTION

The following description describes examples in which an electrical conductivity of a channel 4 is modified as a consequence of modifying resonance energy transfer (RET). A process that controls electrical conductivity of the channel 4 may be interrupted by modifying resonance energy transfer, for example, by switching resonance energy transfer on or by switching resonance energy transfer off. Resonance energy transfer is a process by which energy is transferred between moieties that are in close proximity and that have an emission spectrum for a RET donor moiety that overlaps an absorption spectrum for a RET acceptor moiety. The resonance energy transfer can therefore be controlled by controlling the addition or removal of such moieties.

The invention may also find application as a detector for the presence of an analyte. The analyte may, for example, be a moiety that operates as a RET donor or RET acceptor or be labeled with a moiety that operates as a RET donor or RET acceptor. Alternatively, the analyte may be a moiety that enables RET or disables RET or otherwise affects the efficiency of RET. Such a detector is particularly advantageous as the presence of the analyte is detectable via a change in electrical conductivity of the channel 4 which is straightforward to detect, less subject to interference and has a high signal-to-noise ratio.

Figure 1:
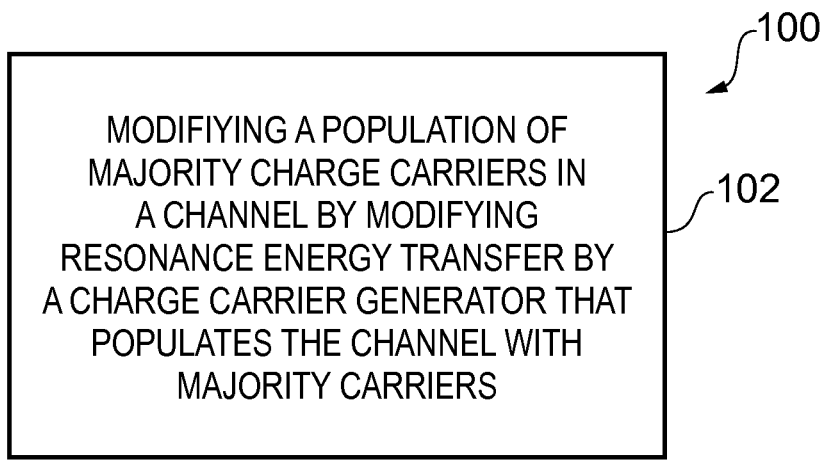
FIG. 1 illustrates an example of a method.

FIG. 1 illustrates an example of a method 100. This method comprises, at block 102, modifying a population of the charge carriers 6 in a channel 4 by modifying resonance energy transfer (RET) by a charge carrier generator 2 that populates the channel 4 with charge carriers 6.

Figure 2:
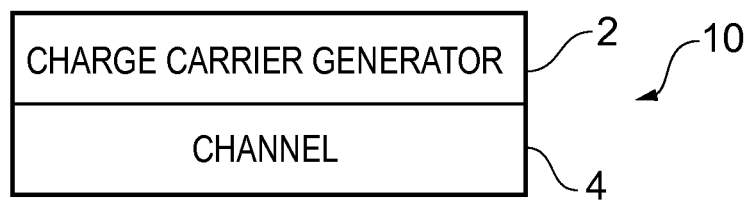
FIG. 2 illustrates an example of an apparatus that comprises a channel and a charge carrier generator.

FIG. 2 illustrates an example of an apparatus 10 that comprises a channel 4 and a charge carrier generator 2. The channel 4 is configured to conduct charge carriers 6 and the charge carrier generator 2 is configured to generate charge carriers 6 for populating the channel 4. The charge carrier generator 2 is additionally configured for resonance energy transfer (RET).

Figure 3A:
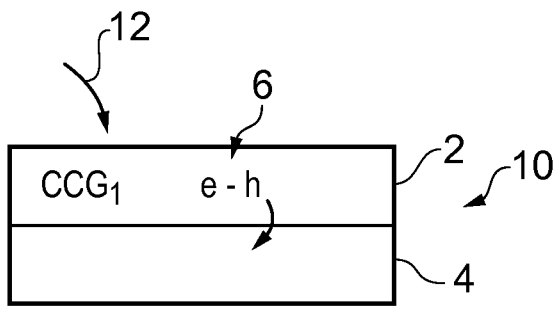
FIGS. 3A and 3B illustrate operation of the apparatus when the charge carrier generator is in a first configuration.
Figure 4:
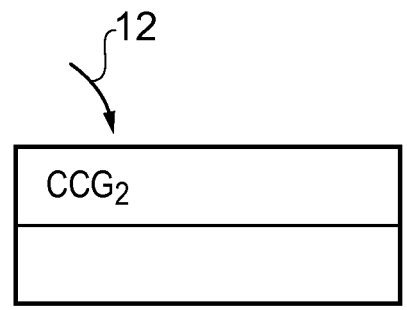
FIG. 4 illustrates operation of the apparatus when the charge carrier generator is in a second configuration different to the first configuration.
Figure 3B:
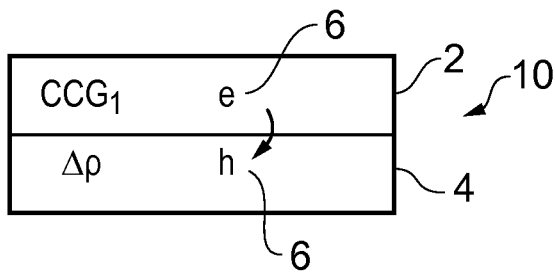

An example of operation of the apparatus 10 is illustrated in FIGS. 3A and 3B and FIG. 4. FIGS. 3A and 3B illustrate operation of the apparatus 10 when the charge carrier generator 2 is in a first configuration and FIG. 4 illustrates operation of the apparatus 10 when the charge carrier generator 2 is in a second configuration different to the first configuration.

Referring to FIG. 3A, an activation 12 provides a stimulus for the creation of charge carriers 6 (creation of charge carrier pairs). In this example, the charge carriers 6 are an electron (e) and a hole (h). The activation 12 may, for example, result in the promotion of an electron from a lower energy level to a higher energy level within the charge carrier generator 2.

As shown in FIG. 3B, a charge carrier 6 may move across a boundary between the charge carrier generator 2 and the channel 4. This movement modifies a population density of the charge carrier in the channel 4 and modifies the electrical conductivity of the channel 4. In the illustrated example, the electron 6 is retained within the charge carrier generator 2 and the hole 6 moves across the boundary to the channel 4. The retained charge carrier gates the channel 4 electrostatically changing the conductivity of the channel 4, This gating effect may last for some time because of the stability of the retained charge carrier.

It will therefore be appreciated that in the first configuration, the charge carrier generator 2 responds to the activation 12 to generate charge carriers 6 that modify the electrical conductivity of the channel 4.

As an example, a band offset between the charge carrier generator 2 and the channel 4 creates a local electric field which acts to ionize the exciton created by the activation 12. One charge carrier, the hole in this example, is attracted (by the electric field) into the channel 4 and the complementary carrier remains in the charge carrier generator 2. The remaining complementary charge carrier gates the channel 4 electrostatically changing the conductivity of the channel 4, This may enable an electric current to flow between source and drain electrodes.

The gain=lifetime of retained charge in charge carrier generator 2/transit time of charge carriers through channel.

Gain can therefore be increased by prolonging the lifetime of retained charge in charge carrier generator 2 and by increasing the mobility of the channel which will decrease transit time of charge carriers through channel.

FIG. 4 illustrates that in the second configuration, the charge carrier generator 2 does not respond to the activation 12 to produce charge carriers 6.

In some but not necessarily all examples, when the charge carrier generator 2 is in one of the first configuration or the second configuration, resonance energy transfer (RET) is enabled and when the charge carrier generator 2 is in the other of the first configuration and the second configuration resonance energy transfer (RET) is disabled.

In some but not necessarily all examples, RET may provide a means by which charge carrier generation occurs. RET is initiated by a donor and this causes charge carrier generation. Removal of the donor inhibits RET and inhibits charge carrier generation. Bioluminescent resonance energy transfer (BRET) is an example of this type of RET.

In some but not necessarily all examples, RET may provide an alternative to charge carrier generation. RET is initiated by addition of an acceptor and this inhibits charge carrier generation. Förster resonance energy transfer (FRET) is an example of this type of RET.

For example in some but not necessarily all examples, bioluminescent resonance energy transfer (BRET) may be enabled when the charge carrier generator 2 is in the first configuration (FIG. 3A). Removal of a bioluminescent resonance energy transfer (BRET) donor moiety from the charge carrier generator 2 changes the configuration of the charge carrier generator 2 from the first configuration to the second configuration (FIG. 4) and disables bioluminescent resonance energy transfer (BRET). In this example, bioluminescent resonance energy transfer (BRET) is the means by which charge carrier generation occurs. The activation 12 activates bioluminescence.

For example in some but not necessarily all examples, Förster resonance energy transfer (FRET) may be disabled when the charge carrier generator 2 is in the first configuration (FIGS. 3A, 3B). Addition of a Förster resonance energy transfer (FRET) acceptor moiety to the charge carrier generator 2 changes the configuration of the charge carrier generator 2 from the first configuration to the second configuration (FIG. 4) and enables Förster resonance energy transfer (FRET). In this example, Förster resonance energy transfer (FRET) is an alternative, preferred means to charge carrier generation. The activation 12 may be photons of a wavelength suitable to cause photo-generation of charge carriers 6 in the charge carrier generator 2.

It will be appreciated that the generated charge carriers 6 comprise a first charge carrier 6 (e.g. an electron) and a second charge carrier (e.g. a hole). The charge carrier generator 2 is configured to trap the first charge carrier (e.g. an electron) but not the second charge carrier (e.g. a hole). As a consequence the second charge carrier (e.g. hole) populates the channel 4. The charge carrier generator 2 may have a work function that is mismatched with the work function of the channel 4.

Figure 5:
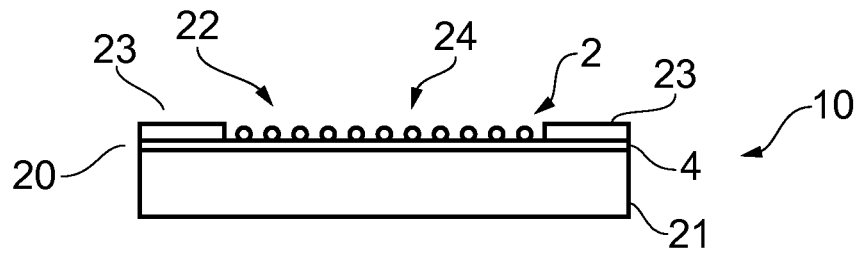
FIG. 5 illustrates an example of the apparatus comprising a channel and a charge carrier generator configured for resonance energy transfer (RET)

FIG. 5 illustrates an example of the apparatus 10 as previously described. It comprises a channel 4 configured to conduct charge carriers 6 and a charge carrier generator 2 configured to generate charge carriers 6 for populating the channel 4 where the charge carrier generator 2 is configured for resonance energy transfer (RET).

In this example, the channel 4 is provided by a material with a very high charge carrier mobility. The material may also be sensitive to field effect to generate a high gain. An example of a suitable material is graphene. For example, a monolayer or bi-layer of graphene 20 may be used as the channel 4. In the illustrated example the layer(s) of graphene 20 is supported on a dielectric substrate 21.

Other suitable materials for the channel 4 include, for example, carbon materials such as graphene, reduced graphene oxide, carbon nanostructures such as carbon nanotubes (CNTs) etc.

Desirable features for the channel are a high surface area to volume ration so that the field effect is high (channel conductivity can be easily influenced), high charge carrier mobility so that the carrier transit time through the channel is small (photoconductive gain is high) and low resistance so that the noise characteristics are good.

In this example, the charge carrier generator 2 is formed from a plurality of quantum dots 24 that have may been functionalized to form functionalized quantum dots 22. The functionalized quantum dots 22 may be, for example, functionalized nanoparticles.

However, in other examples the charge carrier generator 2 may be a moiety that absorbs light strongly creating an exciton which can be ionized by the local electric field formed at the boundary of the charge carrier generator 2 and channel 4 to donate a charge to the channel 4. The remaining charge should remain on the moiety long enough that it gates the passage of many complimentary charge carriers through the channel. Examples of such moieties may include organic dyes (Ruthenium complexes) and 2D materials such as Molybdenum disulphide ($MoS_2$).

A quantum dot 24 may be a cluster of, for example, a few hundred or a few thousand atoms. The atoms may be arranged in binary compounds (e.g. PbS, CdSe, CdTe, GaAs, InAs, AlN, SiC) or in tertiary compounds (InGaN, InGaP, InGaAs.).

A quantum dot 24 may have a size less than 100 nm and in some examples may have a size less than 50 nm or 20 nm. The dimensions of the quantum dot 24 may be controlled to control the quantised energy levels of the quantum dot 24 and fine tune the photo-absorption energies of the quantum dot 24.

Therefore the quantum dots 24 absorb different wavelengths of light depending upon their size (quantum confinement) and their material.

In the example of FIG. 5, electrodes 23 are electrically coupled to the channel 4 to measure the conductivity of the channel 4 or to otherwise detect a change in population of charge carriers in the channel 4 or a change in gating potential.

Figure 6A:
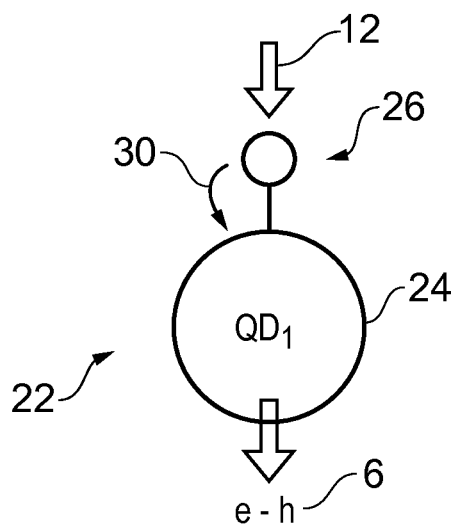
FIGS. 6A and 6B illustrate an example of a functionalized quantum dot of the charge carrier generator in the first configuration (FIG. 6A) and the second configuration (FIG. 6B)
Figure 6B:
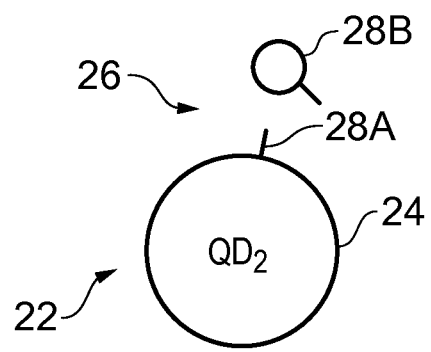

FIGS. 6A and 6B illustrate an example of a functionalized quantum dot 22 of the charge carrier generator 2 in the first configuration (FIG. 6A) and the second configuration (FIG. 6B). In the first configuration, the functionalized quantum dot 22 receives activation 12 and produces charge carriers 6.

Bioluminescent resonance energy transfer (BRET) is enabled when the functionalized quantum dot 22 is in the first configuration (FIG. 6A) and disabled when the functionalized quantum dot 22 is in the second configuration (FIG. 6B).

Bioluminescent resonance energy transfer (BRET) is the channel by which charge carrier generation occurs. The activation 12 activates bioluminescence.

In this example, a functionalized quantum dot 22 comprises a quantum dot 24 comprising a modifiable functionalization 26. The modifiable functionalization 26 under a specific actuation changes from a first configuration as illustrated in FIG. 6A to a second configuration as illustrated in FIG. 6B.

In the first configuration of FIG. 6A, a first moiety 28A and a second moiety 28B are interconnected. The second moiety 28B is connected to the quantum dot 24 via the first moiety 28A and operates as a bioluminescent resonance energy transfer (BRET) donor.

In the second configuration of FIG. 6B, the first moiety 28A remains attached to the quantum dot 24 but the second moiety 28B has been removed or cleaved from the first moiety 28A. The second moiety 28B is therefore no longer able to operate as a bioluminescent resonance energy transfer (BRET) donor to the quantum dot 24 and charge carrier generation does not occur.

Thus removal of a bioluminescent resonance energy transfer (BRET) donor moiety 28B from the functionalized quantum dot 22 changes the configuration of the functionalized quantum dot 22 from the first configuration (FIG. 6A) to the second configuration (FIG. 6B) and disables bioluminescent resonance energy transfer (BRET) inhibiting charge carrier generation.

Although the description of FIGS. 6A and 6B has assumed that the first configuration (FIG. 6A) precedes the second configuration (FIG. 6B), in other examples a transition may instead occur from the second configuration (FIG. 6B) to the first configuration (FIG. 6A).

It is therefore possible to detect the presence of an analyte that is an active moiety in the transition between the first and second configurations or labels an active moiety in the transition between the first and second configurations.

Figure 7A:
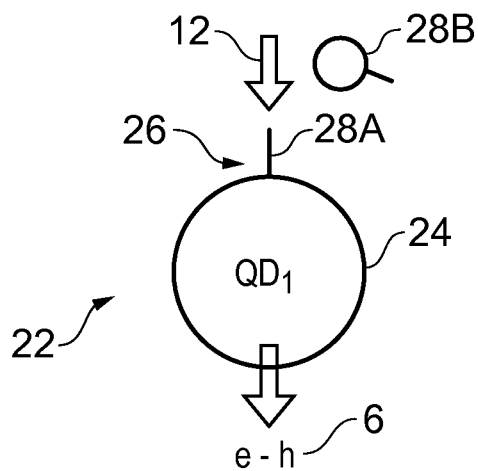
FIGS. 7A and 7B illustrate an example of a functionalized quantum dot of the charge carrier generator in the first configuration (FIG. 7A) and the second configuration (FIG. 7B)
Figure 7B:
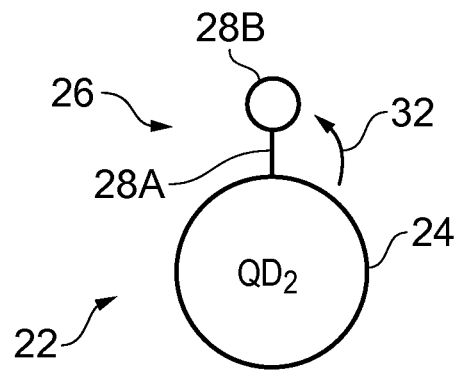

FIGS. 7A and 7B illustrate an example of a functionalized quantum dot 22 of the charge carrier generator 2 in the first configuration (FIG. 7A) and the second configuration (FIG. 7B). In the first configuration, the functionalized quantum dot 22 receives activation 12 and produces charge carriers 6.

Förster resonance energy transfer (FRET) is disabled when the charge carrier generator 2 is in the first configuration (FIG. 7A) and enabled when the functionalized quantum dot 22 is in the second configuration (FIG. 7B). The activation 12 may be photons of a wavelength suitable to cause photo-generation of charge carriers 6 in the charge carrier generator 2 in the first configuration when there is no Förster resonance energy transfer (FRET).

In this example, a functionalized quantum dot 22 comprises a quantum dot 24 comprising a modifiable functionalization 26. The modifiable functionalization 26 under a specific actuation changes from a first configuration as illustrated in FIG. 7A to a second configuration as illustrated in FIG. 7B.

In the first configuration of FIG. 7A, the modifiable functionalization 26 comprises a first moiety 28A attached to the quantum dot 24. A second moiety 28B is not attached to the first moiety 28A.

In the second configuration of FIG. 7B, the modifiable functionalization 26 comprises the first moiety 28A interconnected with the second moiety 28B. The second moiety 28B is connected to the quantum dot 24 via the first moiety 28A and operates as a Förster resonance energy transfer (FRET) acceptor. The second moiety 28B operates as a Förster resonance energy transfer (FRET) acceptor and charge carrier generation does not occur as Förster resonance energy transfer (FRET) provides an alternative, preferred channel to charge carrier generation.

Thus addition of a Förster resonance energy transfer (FRET) acceptor moiety 28B to the functionalized quantum dot 22 changes the configuration of the functionalized quantum dot 22 from the first configuration (FIG. 7A) to the second configuration (FIG. 7B) and enables Förster resonance energy transfer (FRET) inhibiting charge carrier generation.

The acceptor moiety 28B may be selected so that it does not itself create carriers that could gate the channel 4—that is, it should have a very short-lived excited state that e.g. promptly decays radiatively via emission of a photon.

Although the description of FIGS. 7A and 7B has assumed that the first configuration (FIG. 7A) precedes the second configuration (FIG. 7B), in other examples a transition may instead occur from the second configuration (FIG. 7B) to the first configuration (FIG. 7A).

It is therefore possible to detect the presence of an analyte that is an active moiety in the transition between the first and second configurations or labels an active moiety in the transition between the first and second configurations.

Figure 8A:
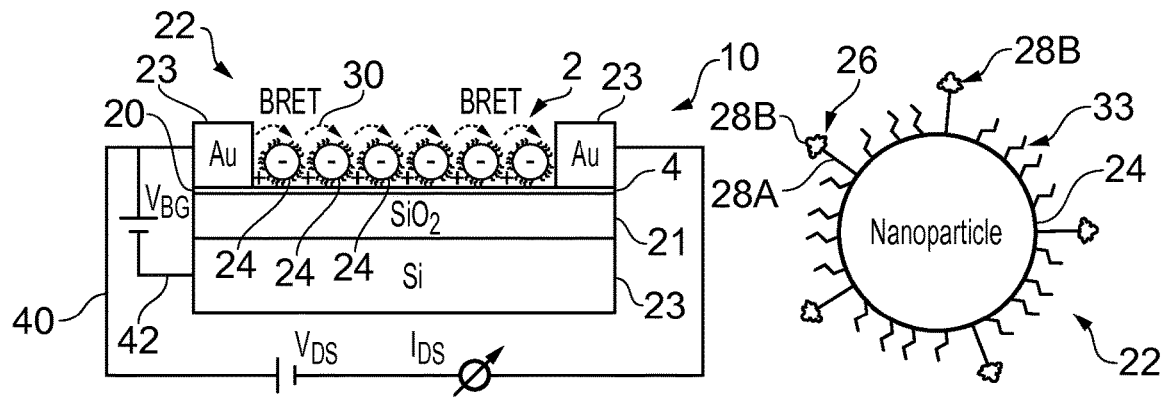
FIGS. 8A and 8B illustrate the application of functionalized quantum dots, for example as illustrated in respective FIGS. 6A and 6B to the apparatus as illustrated in FIG. 5.
Figure 8B:
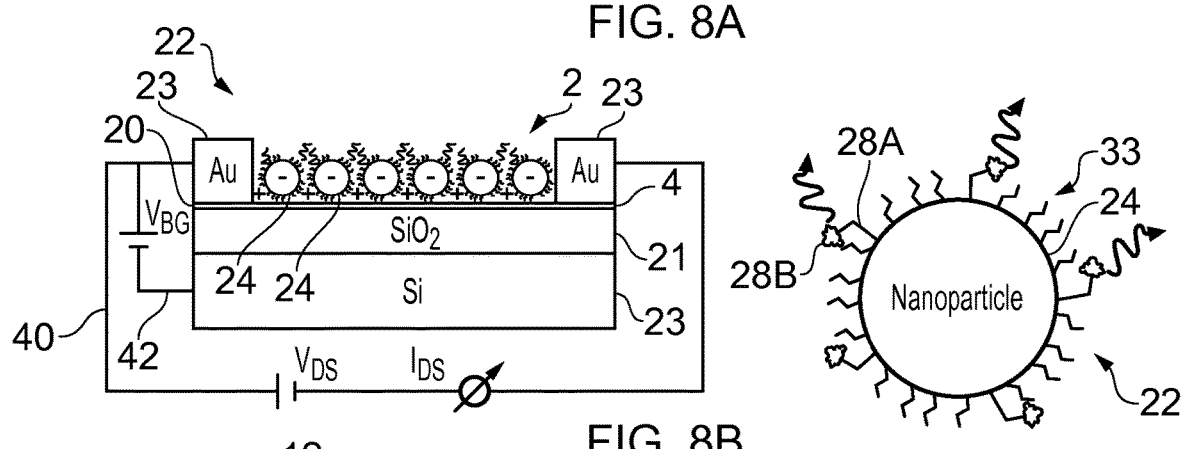

FIGS. 8A and 8B illustrate the application of functionalized quantum dots 22, for example as illustrated in respective FIGS. 6A and 6B to the apparatus 10 as illustrated in FIG. 5.

In FIGS. 8A and 8B, the apparatus 10 is illustrated to the left and the functionalized quantum dot 22 is illustrated to the right. In this example, the second moiety 28B is luciferase.

In the first configuration of FIG. 8A, a probe (first moiety 28A) and luciferase (a second moiety 28B) are interconnected. The luciferase (second moiety 28B) is connected to the quantum dot 24 via the first moiety 28A and operates as a bioluminescent resonance energy transfer (BRET) donor enabling charge carrier generation.

In the second configuration of FIG. 8B, the probe (first moiety 28A) is attached to the quantum dot 24 but the luciferase (second moiety 28B) is not attached to the probe (first moiety 28A). The luciferase (second moiety 28B) does not operate as a bioluminescent resonance energy transfer (BRET) donor to the quantum dot 24 and charge carrier generation does not occur.

The addition of protease may be used as the actuation to detach the luciferase (second moiety 28B) from the probe (first moiety 28A) and change the configuration from the first configuration (FIG. 8A) to the second configuration (FIG. 8B) disabling charge carrier generation.

A detection circuit 40 is used to measure the electrical conductance of the channel 4. It may, for example, measure an electrical current between the electrodes 23 through the channel 4. A change in the measurement may be used, for example, to detect the presence of an analyte that is an active moiety in the transition between the first and second configurations or labels
an active moiety in the transition between the first and second configurations.

In this example, the channel 4 comprises a gate 23. A control circuit 42 may be used to apply a voltage to the gate 23 which is separated from the channel 4 by the dielectric substrate 21. By controlling the voltage applied to the gate 23, the majority carrier type of the channel 4 may be modified and the population of charge carriers in the channel 4 can be controlled. The channel 4 may already have a certain population of charge carriers by virtue of the field effect induced by the gate electrode 23 (as per an FET) when the charge carrier generator generates charge carriers that populate the channel 4.

It will also be appreciated that in the examples of FIGS. 8A and 8B, the functionalized quantum dot 22 is provided by a nanoparticle 24 that has a plurality of molecular capture probes (first moieties) 28A designed to bind to the second moiety 28B. At least some of the sites on the nanoparticle 24 for molecular capture probes (first moieties 28A) are stabilized using a capping agent 33. A capping agent is chosen according to the dispersant (generally a water-buffered solution in which biomolecules do not denature).

Figure 9A:
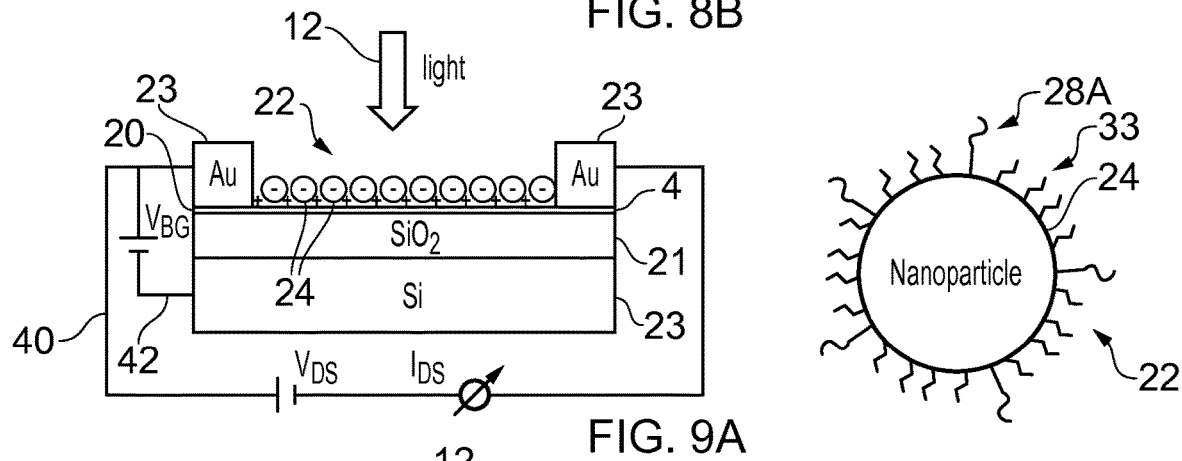
FIGS. 9A and 9B illustrate the application of functionalized quantum dots, for example as illustrated in respective FIGS. 7A and 7B to the apparatus as illustrated in FIG. 5.
Figure 9B:
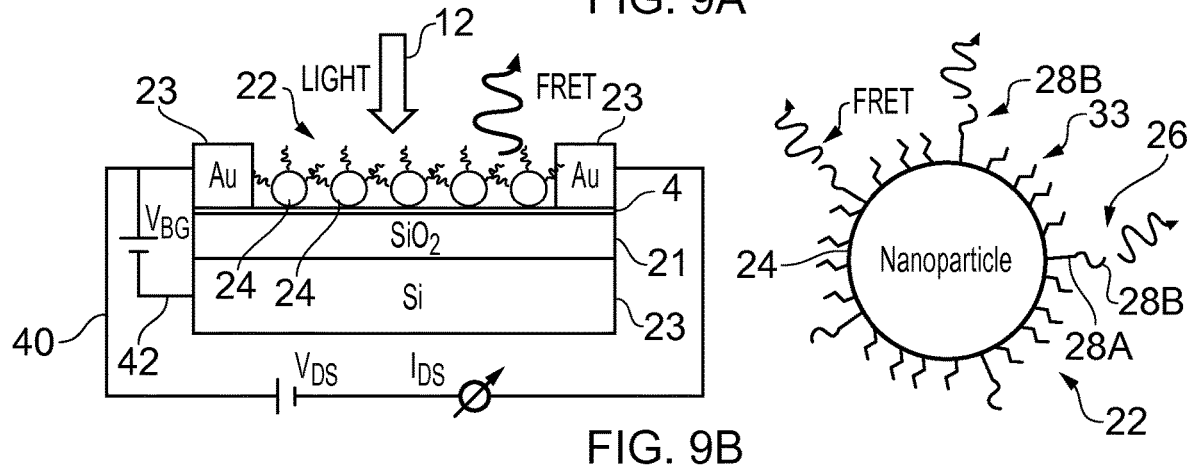

FIGS. 9A and 9B illustrate the application of functionalized quantum dots 22, for example as illustrated in respective FIGS. 7A and 7B to the apparatus 10 as illustrated in FIG. 5.

In FIGS. 9A and 9B, the apparatus 10 is illustrated to the left and the functionalized quantum dot 22 is illustrated to the right.

In the first configuration of FIG. 9A, the probe (first moiety 28A) is attached to the quantum dot 24 but the second moiety 28B is not attached to the probe (first moiety 28A). The second moiety 28B does not operate as a Förster resonance energy transfer (FRET) acceptor and charge carrier generation does occur.

In the second configuration of FIG. 9B, a probe (first moiety 28A) and a second moiety 28B are interconnected. The second moiety 28B is connected to the quantum dot 24 via the first moiety 28A and operates as a Förster resonance energy transfer (FRET) acceptor disabling charge carrier generation. The FRET acceptor also emits light.

A detection circuit 40 is used to measure the electrical conductance of the channel 4. It may, for example, measure an electrical current between the electrodes 23 through the channel 4. A change in the measurement may be used, for example, to detect the presence of an analyte that is an active moiety in the transition between the first and second configurations or labels
an active moiety in the transition between the first and second configurations.

In this example, the channel 4 comprises a gate 23. A control circuit 42 may be used to apply a voltage to the gate 23 which is separated from the channel 4 by the dielectric substrate 21. By controlling the voltage applied to the gate 23, the majority carrier type of the channel 4 may be modified and the population of carriers in the channel 4 can be controlled.

It will also be appreciated that in the examples of FIGS. 9A and 9B, the functionalized quantum dot 22 is provided by a nanoparticle 24 that has a plurality of molecular capture probes (first moieties) 28A designed to bind to the second moiety 28B. At least some of the sites on the nanoparticle 24 for molecular capture probes (first moieties 28A) are stabilized using a capping agent 33. A capping agent is chosen according to the dispersant (generally a water-buffered solution in which biomolecules do not denature).

Figure 10:
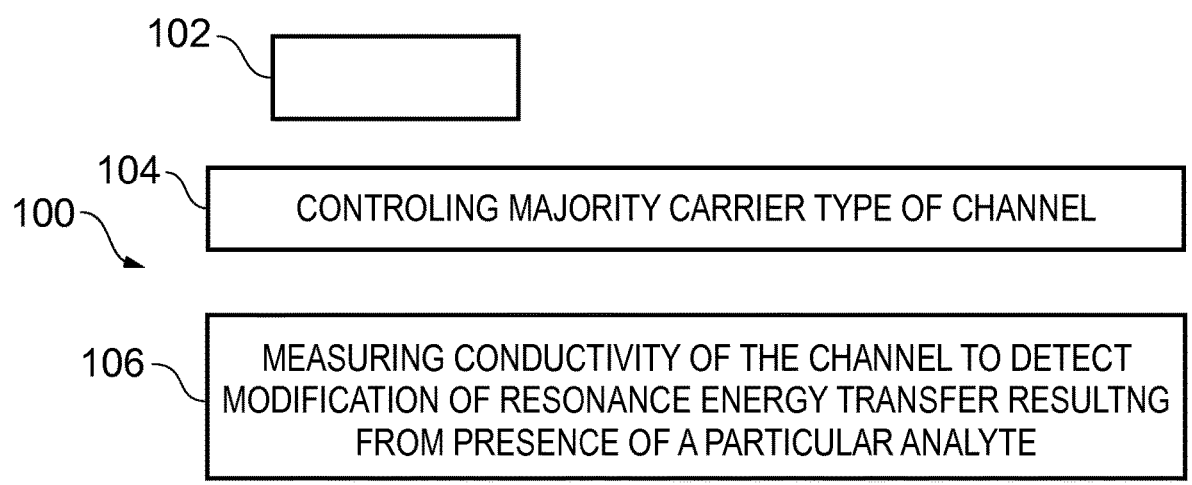
FIG. 10 illustrates an example of a method.

FIG. 10 illustrates another example of the method 10 illustrated in FIG. 1. As illustrated in FIG. 1 it comprises the block 102 in which a population of majority charge carries 6 in a channel 4 is modified by modifying resonance energy transfer (RET) by a charge carrier generator 2 that populates the channel 4 with charge carriers 6.

In this example the method 100 may optionally also comprise the block 104. In this block, the control circuitry 42 illustrated in FIGS. 8A, 8B, 9A, 9B is used to control the majority charge carrier type and/or charge carrier density in the channel 4.

The method 100 may optionally also comprise block 106 comprising measuring the conductivity of the channel 4 using control circuitry 40 illustrated in FIGS. 8A, 8B, 9A, 9B to detect a modification of resonance energy transfer resulting from presence of a particular analyte.

It should be appreciated that the apparatus 10 may be used as a sensor that utilizes RET without the use of optical components such as mirrors, filters and detectors. Consequently the apparatus 10 is much simpler and less expensive. The apparatus 10 may be portable and may be integrated into another apparatus.

Where the material of the channel 4 is graphene, the sensor will be very sensitive and may be capable of measuring a very small concentration of analyte. This is because of the very high photoconductive gain of the graphene-quantum dot system.

In an example, a protease or other enzyme may be used to break a polypeptide chain changing the configuration of a functionalized quantum dot 22 by detaching a portion of the polypeptide chain from the functionalized quantum dot 22 that is or is labelled with a second moiety 28B. The second moiety 28B may be a flurophore and operates as a Förster resonance energy transfer (FRET) acceptor and its detachment enables charge carrier generation (FIG. 7A). Alternatively, the second moiety 28B may operate as a bioluminescence resonance energy transfer (BRET) donor and its detachment disables charge carrier generation (FIG. 6B).

In another example, a protein kinase, polymerase or other enzyme may be used to add a second moiety 28B to a functionalized quantum dot 22 thereby changing its configuration. The second moiety 28B may be a fluorophore and operates as a Förster resonance energy transfer (FRET) acceptor and its attachment disables charge carrier generation (FIG. 7B). Alternatively, the second moiety 28B may operate as a bioluminescence resonance energy transfer (BRET) donor and its attachment enables charge carrier generation (FIG. 6A). FRET may occur when the charge carrier generator 2 comprises a plurality of functionalized quantum dots 22 that have probes (attached first moieties 28A) of avidin. This may be achieved using a streptavidin-conjugated quantum dot (QD). A capture probe labeled with biotin and a reporter probe labeled with cyanine dye (e.g. Cy5) hybridize to a target DNA and form a sandwich hybrid comprising the biotin and Cy5. The hybrids self-assemble onto the surface of the quantum dot 24 as the biotin of the hybrid interacts with the avidin of the functionalized quantum dot 22. The hybrid forms the second moiety 28B and operates as a Förster resonance energy transfer (FRET) acceptor emitting light and preventing charge carrier generation. The activation 12 may be a 488-nanometer-wavelength laser or blue LED. The functionalized quantum dot 24 in the second configuration, via the FRET, emits light at 675 nm via the attached hybrid instead of producing charge carriers 6.

In another example, a 530 nm quantum dot is functionalized using ~10 maltose binding proteins (MBP), each monolabeled with Cy3 and cysteine 95 (maximum absorption ~556 nm, maximum emission ~570 nm). β-CD-Cy3.5 (maximum absorption ~575 nm, maximum emission ~595 nm) are attached to form a QD-10MBP-Cy3-β-CD-Cy3.5 functionalized quantum dot 22. Excitation of the functionalized quantum dot 22 results in FRET excitation of the MBP-Cy3 which in turn FRET excites the β-CD-Cy3.5. Added maltose displaces β-CD-Cy3.5 leading to increased Cy3 emission and a change in charge carrier generation.

In another example, a bioluminescence protein renilla luciferase (Luc8) may be used as a second moiety 28B that operates as a bioluminescence resonance energy transfer (BRET) donor.

According to an example a target substrate and a tag are fused to Luc8. The resulting combination functionalizes a quantum dot 24 via the tag which brings the Luc8 complex close to the quantum dot 24. Upon the addition of Luc8 substrate coelenterazine (in the presence if Ni2+ ions) bioluminescence from Luc8 occurs enabling BRET (FIG. 6A). The combination functionalization may be modified by for example digesting the target substrate using a target enzyme to change the configuration of the quantum dot and remove the second moiety 28B (FIG. 6B). An example of a tag is polyhisitidine and an example of the target is matrix metalloproteinases (MMP-2).

It will be appreciated that it is possible to detect the presence of an analyte that is active in controlling the transition between (to/from) the first and second configurations. The analyte may cause or encourage attachment/detachment of the second moiety 28B. The analyte may prevent or discourage attachment/detachment of the second moiety 28B. The analyte may be or may label the second moiety 28B. The analyte may be or may label the first moiety 28A. The second moiety 28B may operate as a BRET donor. The second moiety 28B may operate as a FRET acceptor. The first moiety 28A may enable attachment of the second moiety 28B to a quantum dot 24.

The above examples may find application in the detection of physical analytes such as, for example, organic compounds, inorganic compounds or species, water-soluble molecules, toxins, small molecule explosives, carbohydrates, ionic species, biomolecules, DNA, proteins, peptides etc.

It will be appreciated that the apparatus 10 as described above in some examples operates as an analyte-sensitive photo-transistor.

Where a structural feature has been described, it may be replaced by means for performing one or more of the functions of the structural feature whether that function or those functions are explicitly or implicitly described.

As used here 'module' refers to a unit or apparatus that excludes certain parts/components that would be added by an end manufacturer or a user. The apparatus 10 may be a module.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
   a substrate;
   a material having a high charge carrier mobility, said material being supported on said substrate;
   a conductive channel in said material;
   at least two electrodes separated from one another along said conductive channel to detect at least one change in a population of charge carriers in the channel; and
   a charge carrier generator overlying said conductive channel and being provided to generate charge carriers for populating the conductive channel, the charge carrier generator including a plurality of quantum dots capable of resonance energy transfer, wherein the plurality of quantum dots have at least one modifiable functionalization, the modifiable functionalization changing under actuation between a first configuration and a second configuration, the change in configuration controlling the resonance energy transfer whereby charge carrier generation by the charge carrier generator is modified to affect an electrical conductivity of the conductive channel.

2. The apparatus as claimed in claim 1, wherein the generated charge carriers comprise a first charge carrier and a second charge carrier and wherein the charge carrier generator is configured to trap the first charge carrier but not the second charge carrier, wherein the second charge carrier populates the channel.

3. The apparatus as claimed in claim 1, wherein the charge carrier generator is configured to photo-generate charge carriers for populating the channel.

4. The apparatus as claimed in claim 1, wherein modifiable functionalization before actuation is configured to cause resonance energy transfer and wherein actuation disables resonance energy transfer.

5. An apparatus as claimed in claim 1, wherein modifiable functionalization before actuation is configured not to cause resonance energy transfer and wherein the actuation enables resonance energy transfer.

6. The apparatus as claimed in claim 1, wherein the charge carrier generator has a work function that is mismatched with a work function of the channel.

7. The apparatus as claimed in claim 1, wherein each of the quantum dots comprises a plurality of modifiable functionalizations for controlling resonance energy transfer.

8. The apparatus as claimed in claim 7, wherein at least some of the modifiable functionalizations are capped using a capping agent.

9. The apparatus as claimed in claim 1, wherein the channel is comprised of a material with a charge carrier mobility at least of an order of at least one of graphene, reduced graphene oxide, and carbon nanostructures.

10. The apparatus as claimed in claim 1, wherein the channel is formed from carbon material.

11. The apparatus as claimed in claim 1, wherein a modification of the resonance energy transfer at the charge carrier generator in the presence of an analyte is used to detect the presence of the analyte based on an observed effect on the electrical conductivity of the conductive channel.

* * * * *